United States Patent [19]

Drago et al.

[11] Patent Number: 4,845,064

[45] Date of Patent: Jul. 4, 1989

[54] CATALYSTS FOR THE PREPARATION ALKYL HALIDES

[75] Inventors: Russell S. Drago; Cindy S. Goldstein, both of Gainesville, Fla.

[73] Assignee: University of Florida, Gainesville, Fla.

[21] Appl. No.: 753

[22] Filed: Jan. 6, 1987

[51] Int. Cl.$^4$ ............... B01J 27/06; B01J 27/125; B01J 27/10; C07C 17/00

[52] U.S. Cl. ............... 502/64; 502/66; 502/174; 502/202; 502/207; 502/227; 502/230; 502/231; 570/240

[58] Field of Search ............... 502/174, 64, 66, 227, 502/230, 231, 202

[56] References Cited

U.S. PATENT DOCUMENTS

| | | | |
|---|---|---|---|
| 3,083,246 | 3/1963 | Holzman et al. | 502/174 |
| 4,413,151 | 11/1983 | Michaelson et al. | 502/174 |
| 4,538,011 | 8/1985 | Drago et al. | 570/240 |
| 4,719,190 | 1/1988 | Drago et al. | 502/227 |

Primary Examiner—Paul E. Konopka
Attorney, Agent, or Firm—Dennis P. Clarke

[57] ABSTRACT

Catalysts for the preparation of alkyl halides produced by reacting (1) transition metal carbonyl complex capable of oxidatively adding $H_2$ or HCl and (2) a Lewis acid from the group consisting of aluminum halides, antimony halides and mixtures thereof, with an adsorbent solid containing surface hydroxyl groups, in a solvent.

7 Claims, 1 Drawing Sheet

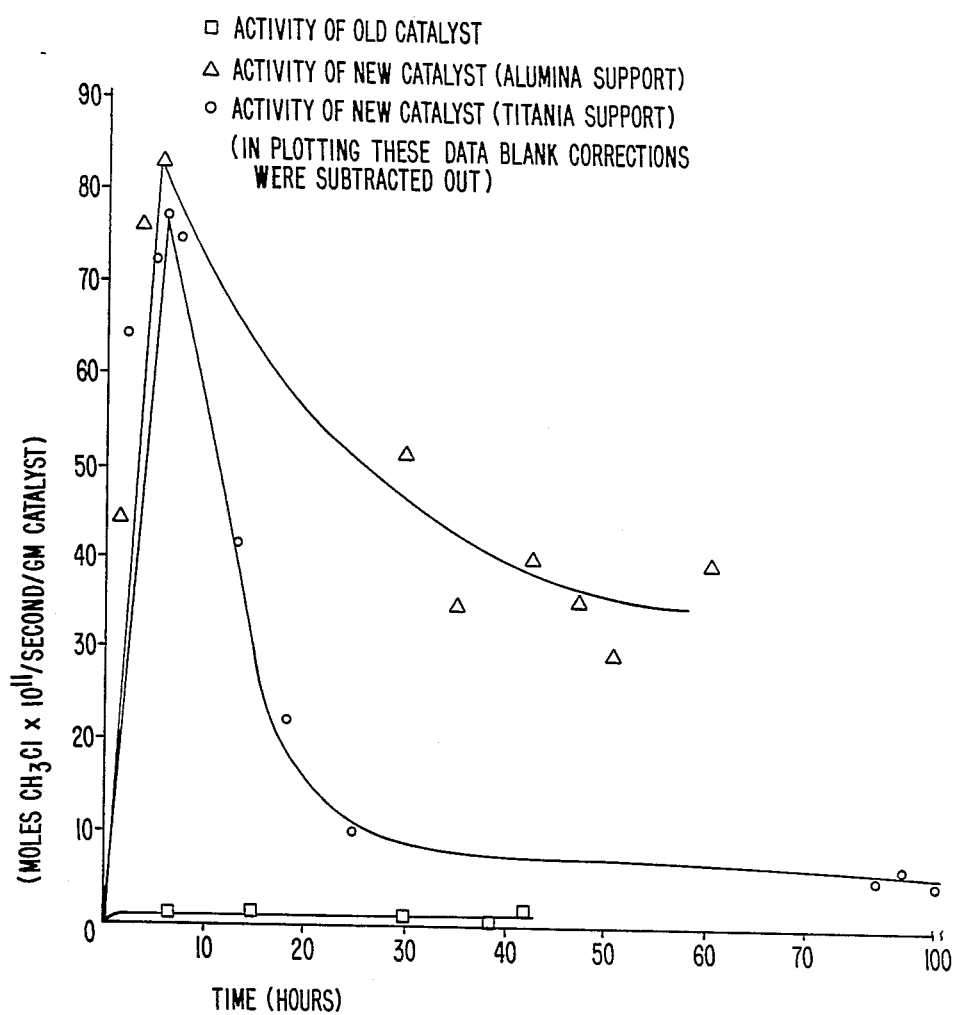

CATALYSTS FOR THE PREPARATION ALKYL HALIDES

BACKGROUND OF THE INVENTION

1. Field of the Invention

The present invention relates to a method for the preparation of certain alkyl halides by the reaction between carbon monoxide and hydrogen (synthesis gas) and a hydrohalide in the presence of a novel catalyst under mild conditions.

2. Prior Art

Until recently, two principal methods were employed industrially for the synthesis of methyl halides. One method involves the chlorination of methane and the other relies on the reaction between methanol and a hydrogen halide. The latter process is the most widely employed and accounts for most of the methyl chloride production in the world. This method produces methyl halide as the sole product of reaction whereas the halogenation of methane typically yields mixtures of methyl halide, methylene halide, haloform and carbon tetrahalide.

Both of these procedures, however, require the utilization of relatively high temperatures and, typically, high pressures, to achieve acceptable yields. These rigorous reaction condition requirements necessitate the use of expensive equipment and not infrequent shutdowns for repair and replacement thereof due to the deleterious effects of hydrogen halide thereon at elevated temperatures. Such necessary demands on the system used for synthesis of the methyl halides contribute to the high cost of methyl halide in the marketplace.

U.S. Pat. No. 4,041,087 describes a method for the preparation of halogenated hydrocarbons, including methyl halides, by reacting carbon monoxide, hydrogen and a source of halogen in the presence of a particular catalyst at temperatures from 200° to 1000° C., preferably 200° -700° C. and at pressures from 0.1 to 500 atm, most preferably 1 -10 atm. In the examples of preferred embodiments set forth in the patent, temperatures of 270° C. and above are employed. The catalyst is described as one of several specific Group VIII metals or alloys (rhenium, platinum-iridium and platinum-rhenium) in combination with an acidic inorganic oxide material.

Although the patented method represents a new approach to the preparation of halogenated hydrocarbons, it also requires the utilization of substantially the same rigorous conditions employed in typical prior art methods. As a result, the costs of halogenated hydrocarbons produced according to the patented method remain relatively high.

Recently, a method was patented (U.S. Pat. No. 4,538,011) for preparing methyl halide or mixtures of methyl halide and ethyl halide by reacting CO, $H_2$ and HX at a temperature below 200° C. in the presence of a catalyst comprising a metal carbonyl complex capable of oxidatively adding hydrogen or HX having the formula $M_n(CO)_m$ wherein M is a transition metal, n and m may be the same or different and are integers having a value of at least 1, in association with (1) at least one Lewis or Bronsted acid capable of coordinating the oxygen atom of said carbonyl moiety and (2) at least one Lewis base other than CO attached to the metal of the metal carbonyl complex having the formula $Z_y[M_n(CO)_m y-]$ wherein M, n and m have the meanings set forth above, y is an integer having a value of at least 1 and Z is a cation or a cationic support ionically bonded to or in association with the transition metal anion.

The patented method produces large amounts of desired product at temperatures between 20° and 100° C. thereby greatly reducing the overall cost of the apparatus and systems required for handling the reactants and conducting the reaction and lessening the cost of the product.

The present invention is an improvement over that described in U.S. Pat. No. 4,538,011.

BRIEF DESCRIPTION OF THE DRAWINGS

FIG. 1 depicts activity curves for various catalysts described herein.

SUMMARY OF THE INVENTION

One embodiment of the invention comprises a method for the preparation of a member selected from the group consisting of $CH_3X$, $CH_3CH_2X$, $CH_3CH_2CH_2X$, $CH_3CH(X)CH_3$ and mixtures thereof wherein X is a halogen selected from the group consisting of chlorine, bromine, fluorine and iodine comprising contacting CO, $H_2$ and HX at a temperature below about 200° C. in the presence of a catalytic amount of a catalyst comprising the product produced by reacting:

(1) a metal carbonyl complex having the formula $M_n(CO)_m$ wherein M is a transition metal, n and m are the same or different and are integers having a value of at least 1, the complex being capable of oxidatively adding $H_2$ or HCl, and (2) a Lewis acid selected from the group consisting of aluminum halides, antimony halides and mixtures thereof, with an adsorbent solid containing surface hydroxyl groups; the reaction of the adsorbent solid with the metal carbonyl complex being effected in an organic solvent and the reaction of the adsorbent solid with the Lewis acid being effected in a solvent selected from the group consisting of $CCl_4$, $CHCl_3$ and mixtures thereof.

A further embodiment of the invention comprises the catalysts prepared as described above.

DETAILED DESCRIPTION OF THE INVENTION

The present invention is predicated on the discovery that the above-described catalysts are significantly more active than those described in U.S. Pat. No. 4,538,011 for preparing methyl halides ($CH_3X$) or mixtures of $CH_3$ and $XCH_2-CH_3$ from CO, $H_2$ and HCl.

The adsorbent solid may be reacted with the metal carbonyl complex prior to, simultaneously with or subsequent to the reaction thereof with the Lewis acid.

The reaction of the adsorbent solid with the metal carbonyl complex may be effected in any suitable solvent for the complex, e.g., benzene, toluene, xylenes, hexanes, carbon tetrachloride, etc.

The reaction between the adsorbent solid and metal carbonyl complex may be carried out at any suitable temperature between about 25° C. and 110° C. The product is then separated and dried prior to reaction with the Lewis acid.

The reaction between the adsorbent solid/metal carbonyl complex reaction product or adsorbent solid and Lewis acid may be effected at any suitable temperature between about 25° C. and about 75° C. in a $CCl_4$, $CH_3Cl$ or $CCl_4/CH_3Cl$ solvent.

While it is in no way intended to limit the invention by the soundness or accuracy of any theories set forth herein to explain the nature of the active catalyst species, it is postulated that, under the conditions of the reaction and because of the nature of the reaction mixture, the aluminum and/or antimony halide molecules react with the surface hydroxyl groups of the absorbent surface to form tetrahedral metal halide groups ($AlX_2$ or $SbX_4$ wherein X is a halide) thereon. It is further postulated that the tetrahedral structure of the metal halide groups bound to the absorbent surface give rise to an unexpectedly high degree of catalytic activity.

It is critical to the success of the invention that the catalyst be prepared employing the halogenated solvents listed above for reaction between the adsorbent solid and the Lewis acid. The utilization of other solvents or the elimination of solvents altogether result in the formation of products having significantly decreased activities.

It is also critical to the success of the invention that the reaction with the Lewis acid be carried out at relatively mild temperature conditions inasmuch as exposure of the active catalyst to temperatures above about 250° C., significantly decreases the activity of the catalyst. Preferably, the reaction is carried out at between about 50° C. and about 75° C. in order to optimize production of the catalyst and avoid decreasing the activity thereof.

Again, it is postulated that the nature of the solvent and the reaction conditions are critically responsible for formation of the tetrahedral structure of the groups which is, in turn, responsible for the high degree of catalytic activity associated with the composite catalyst.

Any transition metal complex capable of undergoing an oxidative addition reaction with hydrogen may be utilized in the catalyst composition employed in the method of the invention. Suitable transition metal complexes are those which undergo the oxidative addition reaction with hydrogen as described in Huheey, Inorganic Chemistry, 3d. Ed., pages 654 –7, (Harper & Rowe, 1983), the disclosure of which is incorporated herein by reference. Exemplary of suitable transition metal catalysts are the nuclearity carbonyl clusters of transition metals such as Ir, Ru, Rh, Co, Fe, Os, Mn, Re, Cr, Mo, W, e.g., $Ir_4(CO)_{12}$, $Ru_3(CO)_{12}$, $Rh(CO)_{16}$, etc. It will be understood that mixture of two or more of the complexes may also be employed.

It has been found that the utilization of certain transition metal carbonyls in the catalyst result in the formation of methyl halides as the sole product whereas the use of other transition metal carbonyls therein favor the formation of mixtures of methyl halides and/or haloethanes and/or halopropanes.

Thus, $Ir(CO)_{12}$ on silica or alumina favor the formation of methyl halides with only trace amounts of ethyl halides.

Catalysts comprising $Ir_4(CO)_{12}$ on titania favor the production of halopropanes (and propane) with trace amounts of methyl and ethyl halides.

Catalysts comprising $Ru_3(CO)_{12}$ on alumina favor halopropanes (and propane) with trace amounts of methyl and ethyl halides.

Catalysts comprising $Rh_6(CO)_{16}$ on alumina favor the formation of mixtures of methyl and ethyl halides.

Exemplary of suitable adsorbent solids having surface hydroxyl groups are silica, alumina, titania, boron oxide, zeolite, magnesia or mixtures thereof.

Following the reactions, the catalyst may be separated from the reaction mixtures according to any conventional procedure for removing solids from liquids, e.g., filtration, centrifugation, etc.

Contact with water and bases should be avoided in order to avoid decomposition or inactivation of the catalyst.

Any aluminum or antimony halide, i.e., chloride, bromide, floride and iodide may be employed in the practice of the invention although it is preferred to use aluminum chloride ($AlCl_3$) or antimony chloride ($SbCl_5$).

A particularly preferred procedure for carrying out the reaction between the adsorbent solid and the Lewis acid involves refluxing a reaction mixture of the adsorbent solid, the Lewis acid and the solvent under an inert atmosphere ($N_2$) the reaction to go to completion, generally in from about 1 hour to about 5 days.

Preferably, the method of synthesis of the alkyl halides is conducted by passing a mixture of synthesis gas (CO and $H_2$) and HX in a closed reactor over a bed or column of the catalyst at a temperature below 200° C., most preferably below about 125° –150° C. at ambient pressure. Any suitable apparatus or system such as those conventionally used for the conversion of synthesis gas may be used for carrying out the method of the invention. See, for example, the system depicted in Schrader et al [J. Mol. Catalysis, 9(2), 179-82 (1980)].

The catalysts of the invention may be readily regenerated after use in syntheses of the above described alkyl halides by reaction of the spent catalyst with a Lewis acid in one of the above described alkyl halide solvents under the aforesaid mild conditions until activity is restored thereto.

The invention is illustrated by the following non-limiting examples.

EXAMPLE 1

In a 200 ml round bottom flask equipped with a reflux condenser was placed 5.0 g alumina (dried at 350° C. under vacuum), 0.55 g $Ir_4(CO)_{12}$ and ~ 100 ml benzene (dried over 4 Å sieves). The mixture was refluxed while stirring for ~ 12 hours. The mixture was filtered and washed with benzene (dried over 4 Å sieves), then dried under vacuum at 25° C. for ~ 12 hours.

In a 200 ml round bottom flask equipped with a reflux condenser was placed 2.0 g of the above-prepared alumina impregnated with $Ir_4(CO)_{12}$, 0.67 g anhydrous aluminum chloride and 100 ml carbon tetrachloride (dried over 4Å sieves). The mixture was allowed to stir at 60° C. under $N_2$ atmosphere for 10 hours. The mixture was filtered and washed with $CCl_4$ under $N_2$ and dried under vacuum at 25° C. for 12 hours.

About 0.5 g of the catalyst composition was loaded into a glass flow reactor. A gas mixture of $H_2$, CO and HCl in a 2:1:0.5 mixture was allowed to flow through the catalyst at 125° C. Gas chromatographic analysis of the product stream revealed methyl chloride. Trace products include methane, ethane and ethyl chloride.

The temperature of the catalyst/reactor zone was increased to 150° C. which resulted in a greater than 10-fold increase in the conversion to methyl chloride.

EXAMPLE 2

The method of Example 1 was repeated utilizing the catalyst composition thereof and flowing a mixture of $H_2$, CO, and HCl in a ratio of 2:1:1. Gas chromatographic analysis of the product stream revealed $CH_3Cl$.

Trace products include $CH_4$ and $C_2H_6$. An increase in temperature to 150° C. resulted in a 10-fold increase in the production of $CH_3Cl$.

EXAMPLE 3

The method of Example 1 was utilized using carbon tetrachloride as the solvent in the reaction step involving adsorption of $Ir_4(CO)_{12}$ onto alumina.

EXAMPLE 4

In a 200 ml round bottom flask equipped with a condenser was placed 4.0 g silica gel (washed with 1M HCl and dried under vacuum at 350° C. for 12 hours). 0.44 g $Ir_4(CO)_{12}$ and 100 ml benzene (dried over 4 Å sieves). The mixture was refluxed while stirring for ~ 12 hours. The mixture was filtered and washed with benzene, then dried at 25° C. under vacuum for ~ 12 hours.

In a 200 ml round bottom flask equipped with a reflux condenser was placed 2.0 g of the silica gel reacted with $Ir_4(CO)_{12}$ and 100 ml carbon tetrachloride. After purging the system with $N_2$, 0.67 g of anhydrous aluminum chloride was added and the mixture was allowed to stir at ~ 70° C. under $N_2$ atmosphere for ~ 12 hours.

About 0.5 g of the catalyst composition was loaded into a glass flow reactor. A gas mixture of $H_2$, CO and HCl in a 2:1:0.5 mixture was allowed to flow through the catalyst at 125° C. Gas chromatography analysis of the product stream revealed methyl chloride as the major product. Trace products include methane, ethane and ethyl chloride.

EXAMPLE 5

In a 200 ml round bottom flask equipped with a condenser was placed 4.0 g silica gel (washed with 1M HCl and dried under vacuum at 80° C.) and ~ 100 ml carbon tetrachloride (dried over 4 Å sieves). After purging the system with $N_2$, 2.0 g anhydrous aluminum chloride ($Al_2Cl_6$) was added and the mixture was allowed to stir at reflux under a $N_2$ atmosphere for two days.

After two days the reaction mixture was cooled and the mixture filtered under $N_2$ atmosphere, then dried under vacuum at 25° C. for ~12 hours.

In a 200 ml round bottom flask equipped with a condenser was placed ~100 ml carbon tetrachloride (dried over 4 Å sieves). After purging with $N_2$, 2.0 g of the above prepared silica gel reacted with anhydrous aluminum chloride of said composition and 0.22 g $Ir_4(CO)_{12}$ was added and the mixture was allowed to stir at 70° C. under $N_2$ atmosphere for ~12 hours. The mixture was filtered and washed with carbon tetrachloride (dried over 4 Å sieves), then dried under vacuum at 25° C. for ~ 12 hours.

About 0.5 g of the catalyst composition was loaded into a glass flow reactor. A gas mixture of $H_2$, CO and HCl in a 2:1:0.5 mixture was allowed to flow through the catalyst at 125° C. Gas chromatographic analysis of the product stream revealed methyl chloride as the major product. Trace products include methane, ethane and ethyl chloride.

EXAMPLE 6

The method of Example 5 was repeated utilizing alumina (dried at 350° C. under vacuum for 6 hours) in place of silica gel. Methyl chloride, methane, ethane, and ethyl chloride were produced at 150° C.

EXAMPLE 7

After several days of exposure of the catalyst in Example 1 to $H_2$, CO and HCl and a decrease in activity of 100-fold, the catalyst was removed from the reactor and mixed with 0.33 g anhydrous aluminum chloride and ~ 100 ml carbon tetrachloride (dried over 4 Å sieves). The mixture was allowed to stir and react at 70° C. for ~ 8 hours. The mixture was filtered and washed with $CCl_4$, then dried for ~ 12 hours at 250° C.

About 0.5 g of the composition catalyst was loaded into a glass flow reactor. A gas mixture of $H_2$, CO and HCl in a 2:1:0.5 mixture was allowed to flow through the catalyst at 150° C. Gas chromatographic analysis of the product stream revealed methane, acetylene, ethylene, propane, methyl chloride, acetaldehyde, ethylchloride, methylene chloride, and 2-chloropropane. The activity was 10-fold more active than the catalyst after being on stream for several days.

EXAMPLE 8

The method of Example 1 was repeated utilizing methylene chloride (dried over 4 Å sieves) in the reaction step with anhydrous aluminum chloride.

A gas mixture of $H_2$, CO and HCl was allowed to flow through the catalyst. Gas chromatographic analysis reveal methane, ethane, methyl chloride, ethyl chloride and methylene chloride as the products.

EXAMPLE 9

The method of Example 5 was repeated utilizing hydroxylated titania (dried at 400° C. under vacuum for ~ 8 hours) in place of silica gel.

About 0.5 g of the catalyst composition was loaded into a glass flow reactor. A gas mixture of $H_2$, CO and HCl was allowed to flow through the catalyst at 125° C. Gas chromatographic analysis revealed propane and 2-chloropropane as the major products. Trace products include methane, ethane, methyl chloride, propene and ethyl chloride.

The temperature of the catalyst/reactor zone was increased to 150° C which resulted in a 100-fold increase in selectivity for propane, 2-chloropropane and methane.

EXAMPLE 10

In a 200 ml round bottom flask equipped with a condenser was placed 3.7 g alumina (dried at 300° C. under vacuum), and 0.3 g ruthenium carbonyl ($Ru_3(CO)_{12}$) and ~ 100 ml benzene (dried over 4 Å sieves). The mixture was allowed to stir and react at 80° C. for ~ 12 hours. The mixture was filtered and washed with benzene (dried over 4 Å sieve) then dried under vacuum at 25° C. for ~ 12 hours.

In a 200 ml round bottom flask equipped with a condenser was placed 4 grams of alumina containing ruthenium carbonyl of said composition, 0.1 g anhydrous aluminum chloride and ~ 100 ml carbon tetrachloride. The mixture was allowed to stir at reflux under $N_2$ atomosphere for ~ 10 hours. The mixture was filtered and washed with carbon tetrachloride (dried over 4 Å sieves), then dried under vacuum at 25° C. for ~12 hours.

About 0.5 g of the composition catalyst was placed in a glass flow reactor. A gas mixture of $H_2$, CO and HCl in a 2:1:1 ratio was allowed to pass through the catalyst. Gas chromatographic analysis of the product stream revealed propane and 2-chloropropane as the major product. Trace products include methane, ethane, ethylene, propene, methyl chloride, ethyl chloride and methylene chloride.

EXAMPLE 11

The method of Example 10 was repeated utilizing rhodium carbonyl in place of ruthenium carbonyl.

About 0.5 g of the composition catalyst was placed in a glass flow reactor tube. A gas mixture of H, CO and HCl was allowed to pass through the catalyst. Gas chromatographic analysis of the product stream revealed methyl chloride, methane, ethane, ethylene, propane, propene, ethyl chloride, and butane.

Referring to the drawing, the FIGURE depicts a comparison of the activities of the catalysts of the present invention with those produced according to the methods described in U.S. Pat. No. 4,538,011. The triangles ($\Delta$) represent the activities of catalysts prepared according to Example 1 above. The squares ($\square$) represent the activities of catalysts prepared according to Example 2 of U.S. Pat. No. 4,538,011. The respective catalysts were employed in the reaction system described in Example 1 above for the preparation methyl chloride.

As is readily apparent from FIG. 1, the catalysts of the present invention are significantly more active than those described in U.S. Pat. No. 4,538,011.

We claim:

1. A catalyst comprising the product produced by reacting at a temperature between about 25° C. and about 110° C. (1) a metal carbonyl complex having the formula $M_n(CO)_m$ wherein M is a transition metal, n and m are the same or different and are integers having a value of at least 1, said complex being capable of oxidatively adding $H_2$ or HCl with an adsorbent solid containing surface hydroxyl groups, and then reacting at a temperature between about 25° C. and about 75° C. the adsorbent solid with (2) a Lewis acid selected from the group consisting of aluminum halides, antimony halides and mixtures thereof in a solvent selected from the group consisting of $CCl_4$, $CHCl_3$ and mixtures thereof.

2. A catalyst comprising the product produced by reacting at a temperature between about 25° C. and about 75° C. an adsorbent solid containing surface hydroxyl groups with (1) a Lewis acid selected from the group consisting of aluminum, antimony halides and mixtures thereof in a solvent selected from the group consisting of $CCl_4$, $CHCl_3$ and mixtures thereof, and then reacting said adsorbent solid with (2) a metal carbonyl complex having formula $M_n(CO)_m$ wherein M is a transition metal, n and m are the same or different and are integers having a value of at least 1, said complex being capable of oxidatively adding $H_2$ or HCl, in an organic solvent at a temperature of between about 25° C. and about 110° C.

3. A catalyst comprising the product produced by simultaneously reacting at a temperature between about 25° C. and about 110° C., (1) a metal carbonyl complex having the formula $M_n(CO)_m$ wherein M is a transition metal, n and m are the same or different and are integers having a value of at least 1, said complex being capable of oxidatively adding $H_2$ or HCl, and (2) a Lewis acid selected from the group consisting of aluminum halides, antimony halides and mixtures thereof, with an adsorbent solid containing surface hydroxyl groups in a solvent selected from the group consisting of $CCl_4$, $CHCl_3$ and mixtures thereof.

4. The catalyst of claim 1, 2, or 3 wherein said transition metal complex is selected from the group consisting of nuclearity carbonyl clusters of transition metals and mixtures thereof.

5. The catalyst of claim 1, 2 or 3 wherein said Lewis acid is aluminum chloride.

6. The catalyst of claim 1, 2 or 3 wherein said Lewis acid is antimony chloride.

7. The catalyst of claim 1, 2 or 3 wherein said adsorbent solid is selected from the group consisting of materials containing silicia, alumina, titania, boron oxide, a zeolite, magnesia or mixtures thereof.

* * * * *

UNITED STATES PATENT AND TRADEMARK OFFICE
CERTIFICATE OF CORRECTION

PATENT NO. : 4,845,064

DATED : July 4, 1989

INVENTOR(S) : RUSSELL S. DRAGO; CINDY S. GOLDSTEIN

It is certified that error appears in the above-identified patent and that said Letters Patent is hereby corrected as shown below:

Claim 2, column 8, line 5, should read:

--group consisting of aluminum halides, antimony halides and --.

Signed and Sealed this

Twenty-seventh Day of February, 1990

*Attest:*

JEFFREY M. SAMUELS

*Attesting Officer*   *Acting Commissioner of Patents and Trademarks*